United States Patent [19]

Gilblom et al.

[11] Patent Number: 5,040,057
[45] Date of Patent: Aug. 13, 1991

[54] MULTI-MODE TDI/RASTER-SCAN TELEVISION CAMERA SYSTEM

[75] Inventors: David L. Gilblom, Los Altos; Jack W. Gittings, Redwood City, both of Calif.

[73] Assignee: Picker International, Inc., Highland Hts., Ohio

[21] Appl. No.: 566,547

[22] Filed: Aug. 13, 1990

[51] Int. Cl.⁵ .............................................. H04N 7/18
[52] U.S. Cl. ................................. 358/101; 358/213.26
[58] Field of Search .................... 358/213.26, 213.27, 358/213.31, 106, 101, 107, 139; 250/572, 578

[56] References Cited

U.S. PATENT DOCUMENTS

| | | | |
|---|---|---|---|
| 4,578,810 | 3/1986 | MacFarlane et al. | 358/106 X |
| 4,591,727 | 5/1986 | Gaebelein, deceased et al. | 358/213.31 X |
| 4,811,106 | 3/1989 | Burt et al. | 358/213.26 |
| 4,811,409 | 3/1989 | Cavan | 358/101 X |

Primary Examiner—Victor R. Kostak
Attorney, Agent, or Firm—Fay, Sharpe, Beall, Fagan, Minnich & McKee

[57] ABSTRACT

Mode selection switches (76, 96, 98) selectively interconnect a sensor line shift timing generator (76) with one of three signal sources - (1) a conventional raster scan timing signal from a raster scan sync generator (70), (2) variable speed external timing signals from a tachometer (32), and (3) fixed speed timing signals developed from the horizontal timing signals of the raster scan sync generator. In a time delay and integration mode, the sensor line shift timing generator causes the CCD arrays of an image section (22) and storage section (24) to shift pixel values down the CCD arrays at a rate commensurate with the external timing signal. As a spot of light emanating from a portion of an object moving through an examination region moves along the CCD array, a corresponding pixel charge is shifted through the CCD array at the same speed such that the same pixel charge integrates light from the same spot as it moves the entire length of the CCD array. An output register timing generator (80) generates timing signals for output registers (26) such that an output signal is produced that is compatible with EIA-170 television signal standard. In the conventional raster scan mode, the camera works as a conventional video camera. When connected to the variable frequency timing signal, the video picture scrolls down the TV monitor clocked by the tachometer in proportion to the speed of the conveyor. In the calibration mode, the image scrolls down the video screen at a fixed rate.

12 Claims, 5 Drawing Sheets

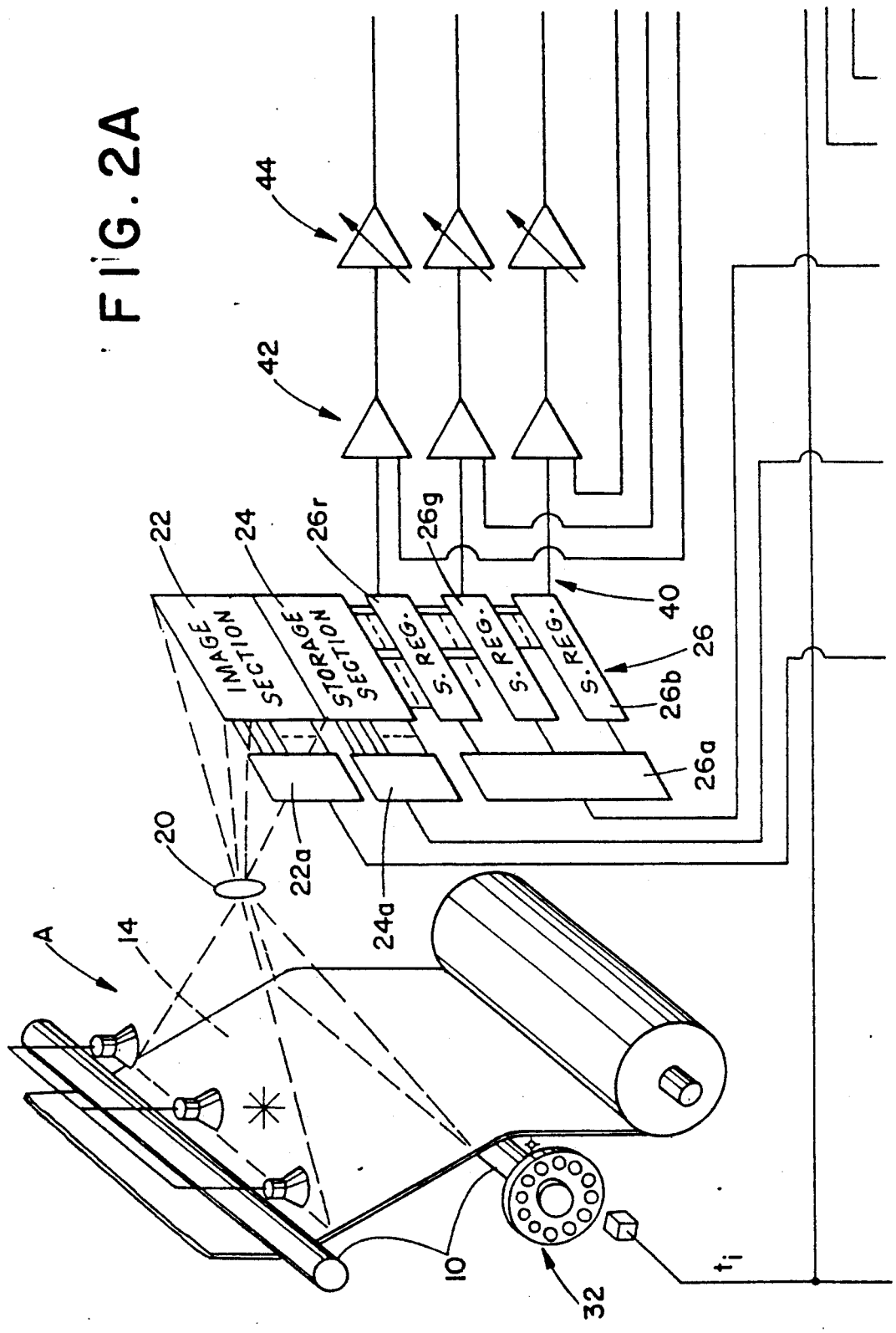

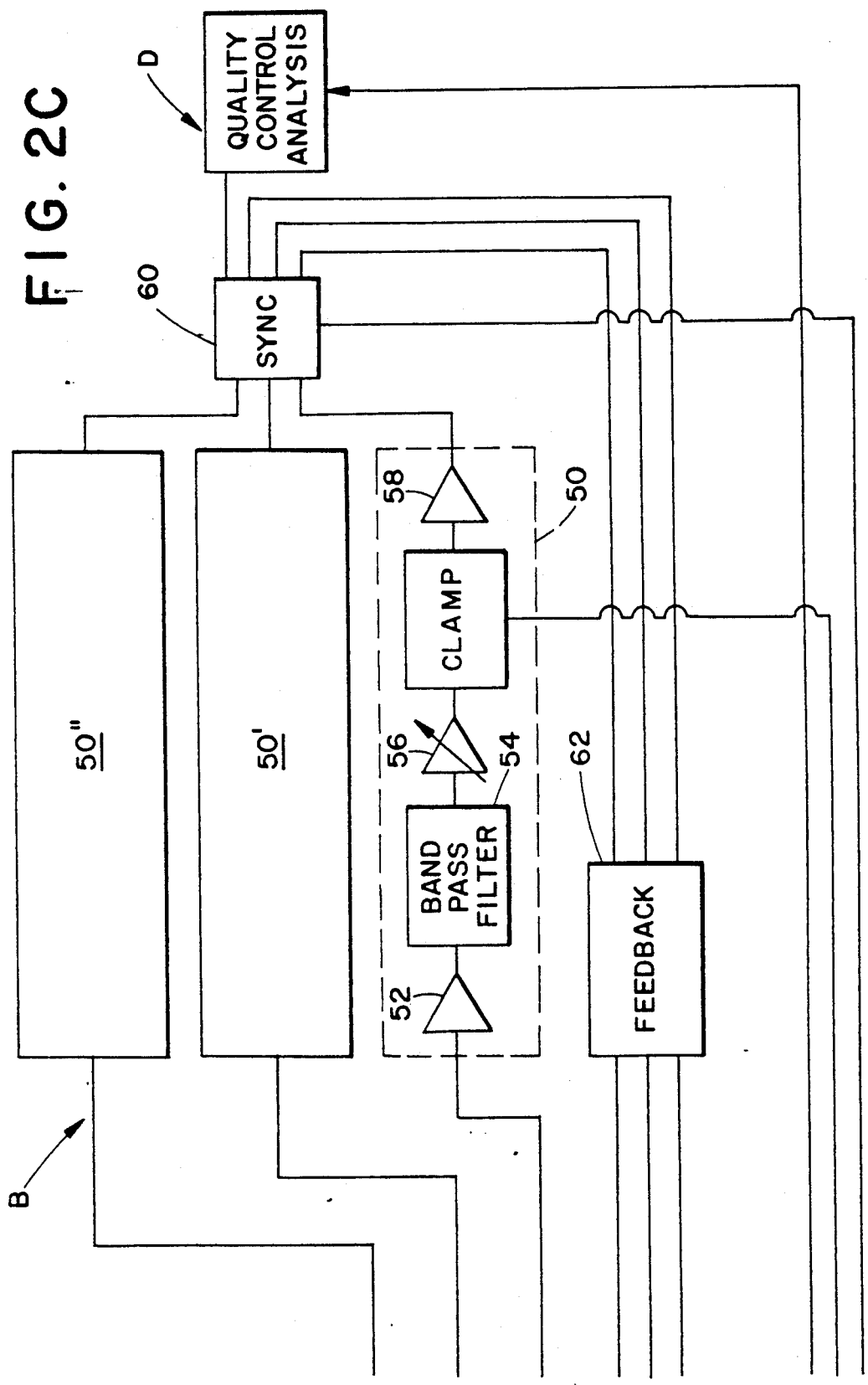

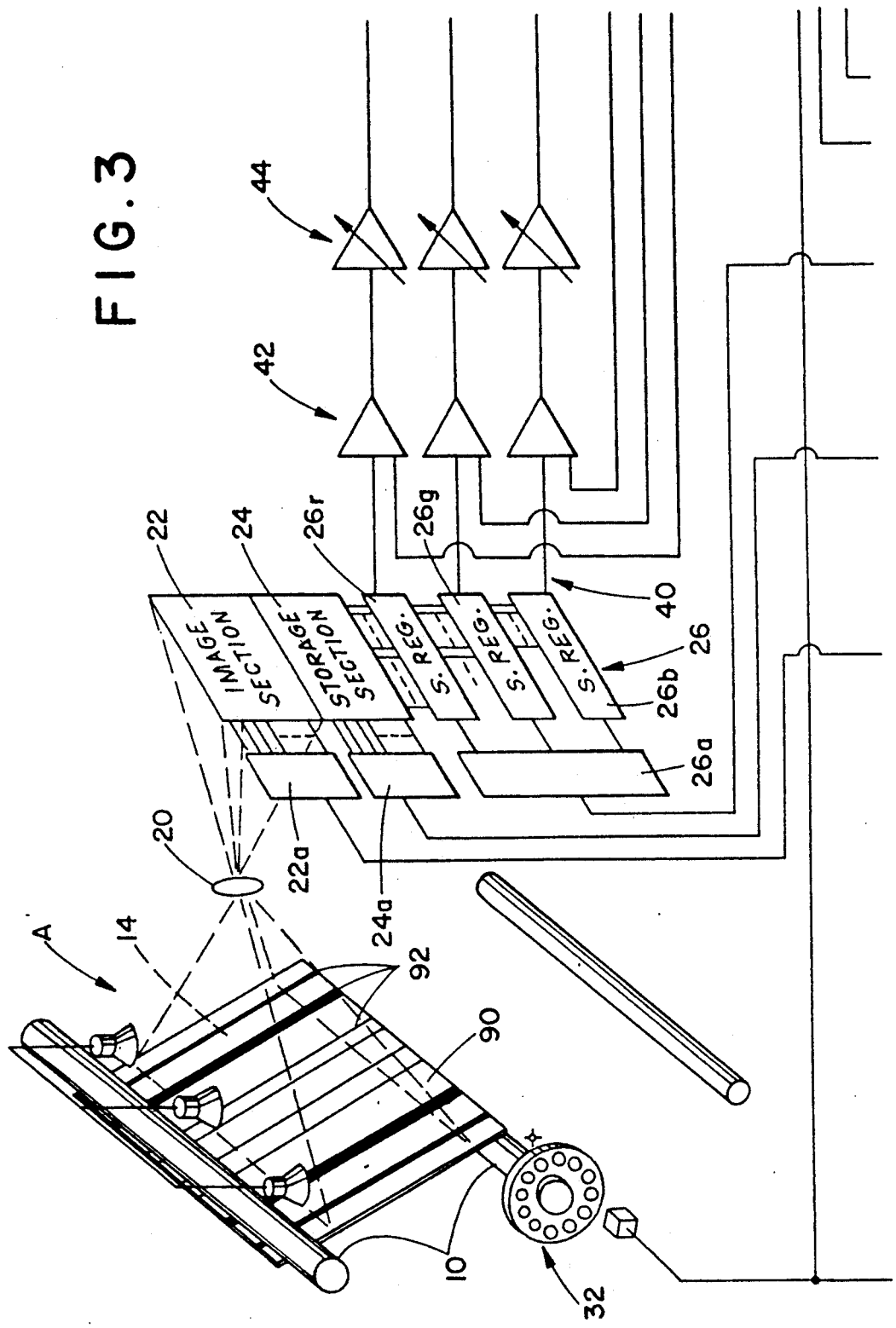

MULTI-MODE TDI/RASTER-SCAN TELEVISION CAMERA SYSTEM

BACKGROUND OF THE INVENTION

The present invention relates to the video camera art. It finds particular application in conjunction with quality control and monitoring with CCD video cameras, especially of continuous material processes, and will be described with particular reference thereto. It is to be appreciated that the invention may be used with CCD and other video cameras for other applications including document recording, photographic film scanning, photographic archival recording, object tracking, video security, and the like.

Heretofore, quality control and monitoring has been carried out with charge coupled devices (CCD) and other video cameras. In one method, a video output signal was generated which included a long, continuous series of video image fields. In a frame transfer CCD camera, light from a continuous or pulsed source was focused on an image section of a CCD sensor for a selected interval of time. The interval was selected to produce good image contrast without significant blurring of the image due to object motion. The charge on each element of the image section was indicative of received light intensity. The charge was transferred during a vertical blanking interval, e.g. a few hundred microseconds, into corresponding elements of an optically insensitive CCD mass storage section. As the image section again commenced integrating received light, the charge was read out element by element from the optically insensitive elements to form a video signal representing one field of the resultant image. After the 1/60th of a second or other selected read out interval, the charge representing the second field was transferred from the image section to the storage section. As the second field was read out of the storage section, the second video signal image section started integrating light to form a third field. This sequence was repeated cyclically to form a video signal representing a series of single image fields.

Continuous production of image fields rendered CCD cameras awkward to adapt for certain high volume quality control situations. As a continuous sheet or individual object was moved past the CCD camera, the resultant video signal represented a long series of image fields. In order to review the images of each object to monitor for a controlled characteristic, it was first necessary to determine which portion of the video signal included the field(s) which represented the monitored individual object or portion of the continuous sheet. Second, it was necessary to determine within the field the actual location of the monitored object or sheet portion. When increased lighting was necessary, the actuation of strobed lighting was coordinated with the field of interest. If the strobe lighting was not completely coincident with a common location of the object or sheet portion within the field(s) of interest, lighting intensities and object shapes would vary among the fields of interest for each object or sheet portion. If the stream of objects or sheet was moving rapidly compared with 1/60th of a second or other one field exposure time, then each object would be in a different position within the selected field of interest. This different positioning of the object not only required identifying the object position in the video field, but could also result in different lighting conditions on the object. These inaccuracies in the timing, positioning, and lighting of the monitored objects all limited the degree of accuracy and the speed with which quality control monitoring could be performed.

In the quality control and monitoring method described in parent U.S. patent application Ser. No. 186,446, filed Apr. 28, 1988, a CCD device is asynchronously triggered at a controlled instant in time to "grab" a moving object. The instant in time is synchronized while the moving object enters to a preselected examination point. A high intensity strobe is flashed concurrently with asynchronously triggering a CCD device to "grab" the moving object. While such a method has certain unique advantages, it requires a significant amount of power capacity to flash the high intensity light necessary for its functioning. The minimum cycle time of the strobe limits the speed of the conveying system.

Although asynchronous triggering is applicable to continuous web monitoring, some webs are advanced at such high speeds that the repower time of the strobe may limit the web advancement speed. Additionally, inspection of continuous webs with cameras producing a series of individual fields requires matching the tops and bottoms of adjacent fields to provide a single complete image of the web without gaps or overlaps. Processes in which continuous webs are advanced include the fabrication of sheets and films of plastics such as polyethylene, MYLAR, cellophane and vinyl, metals, glass, plywood, paper and other wood pulp products, fabrics, printing of newspapers, magazines, wallpaper, packaging, etc., lamination of plastics, composites, paper, etc., coating of plastics, metals, etc. with paint, magnetic particles, abrasives, adhesives, photographic emulsions, electrically conductive materials, etc., and embossing, cutting, slitting, perforating, etc. of any of the aforementioned raw or processed materials.

In the past, some of these webs have been imaged using line-scan cameras, that is, cameras using sensors constructed of a single row of photosensitive areas. The range of application of such sensors has been severely limited due to the low maximum speed at which the web can travel and due to the large amount of illumination necessary to produce usable signals from the sensor. In addition, because line-scan sensors cannot produce images when the web motion is stopped, focusing and alignment of such systems is difficult.

Cameras using the time-delay-and-integration (TDI) scanning mode have been built in the past for military aerial reconnaissance and some other specialized applications. However, these have not been usable in web inspection because they could not be synchronized with the web motion. Their utility was further limited because they could not acquire images unless the object being viewed was moving at the correct velocity relative to the camera. This makes system set-up with static objects nearly impossible.

In the camera system described in parent U.S. patent application Ser. No. 293,960, the camera was operable in either a time delay and integration mode or a standard raster scan mode. However, in the TDI mode, no image was generated when the web stopped moving. This temporary lack of an image had drawbacks in the initial calibration, focusing, and alignment of cameras.

The present invention contemplates a new and improved video camera system and method which overcomes the above referenced problems and others.

SUMMARY OF THE INVENTION

In accordance with the present invention, a multi-mode video camera is provided. A switching means selectively switches between a time delay and integration mode and at least one additional mode.

In accordance with a more limited aspect of the invention, the additional mode utilizes preselected, constant frequency timing signals.

In accordance with a still more limited aspect of the present invention, the switching means selects among at least three modes, the time delayed integration mode, a conventional raster scanning mode, and a time delayed and integration mode in which the camera is clocked by the preselected, fixed frequency timing signal.

In accordance with another aspect of the present invention, a video camera system is provided. A conveying means conveys at least one item to be examined through an examination region. A conveying means speed dependent timing device means generates conveying means speed dependent timing signals that vary in accordance with a speed of the conveying means through an examination region. A lens focuses light from an examination region on a video pick up array. A timing generator means controls the shifting and integration of signal values along the array in accordance with the received timing signals. A switching means selectively switches one of the conveying mean speed dependent timing signals and an internal timing signal to the timing generator means.

In accordance with another aspect of the present invention, a test chart is provided in conjunction with the video camera system. The test chart includes a plurality of stripes along the direction of web movement which is mounted stationarily in the examination region.

A first advantage of the present invention is that it facilitates calibration, focusing, and alignment of cameras in the TDI mode.

Another advantage of the present invention is that it permits calibration signals to be digitized by data acquisition and processing boards that are limited to receiving data at fixed frequencies. This expedites development of examination and inspection algorithms.

Another advantage of the present invention is that it performs scans in a raster mode with static objects, a TDI mode synchronized with object motion, or a TDI mode with a fixed scrolling rate and that any mode may be selected at any time.

Another advantage of the invention is that it allows the rate at which the images are acquired to be controlled directly by the process producing the material to be viewed.

Another advantage of the present invention is that it consume less electrical power than cameras which require high intensity flashes to illuminate the object.

Another advantage of the present invention is that it permits monitoring under lower levels of lighting and non-flashed lighting.

Another advantage of the present invention is that it allows for monitoring of a continuous web process without overlapping. Identifying and recognizing the overlap between frames is eliminated.

Another advantage of the present invention is that it permits the routines used to process the video data when the camera is operating in the TDI mode in a system to be developed in the lab with static objects using the TDI mode.

Yet another advantage of the present invention is that it refreshes pixel light values representing light received by light sensors, throughout the integration period.

Still further advantages of the present invention will become apparent to those of ordinary skill in the art upon reading and understanding of the following detailed description.

BRIEF DESCRIPTION OF THE DRAWINGS

The present invention may take form in various components and arrangements of components or in various steps and arrangements of steps. The figures are only for purposes of illustrating a preferred embodiment and are not to be construed as limiting the invention.

FIGS. 2A, 2B, and 2C taken together are a more detailed illustration of the system of FIG. 1; and, FIG. 3 is an alternate embodiment to FIG. 2A illustrating an alignment, focusing, and calibration test chart.

DETAILED DESCRIPTION OF THE PREFERRED EMBODIMENT

Figure 1:
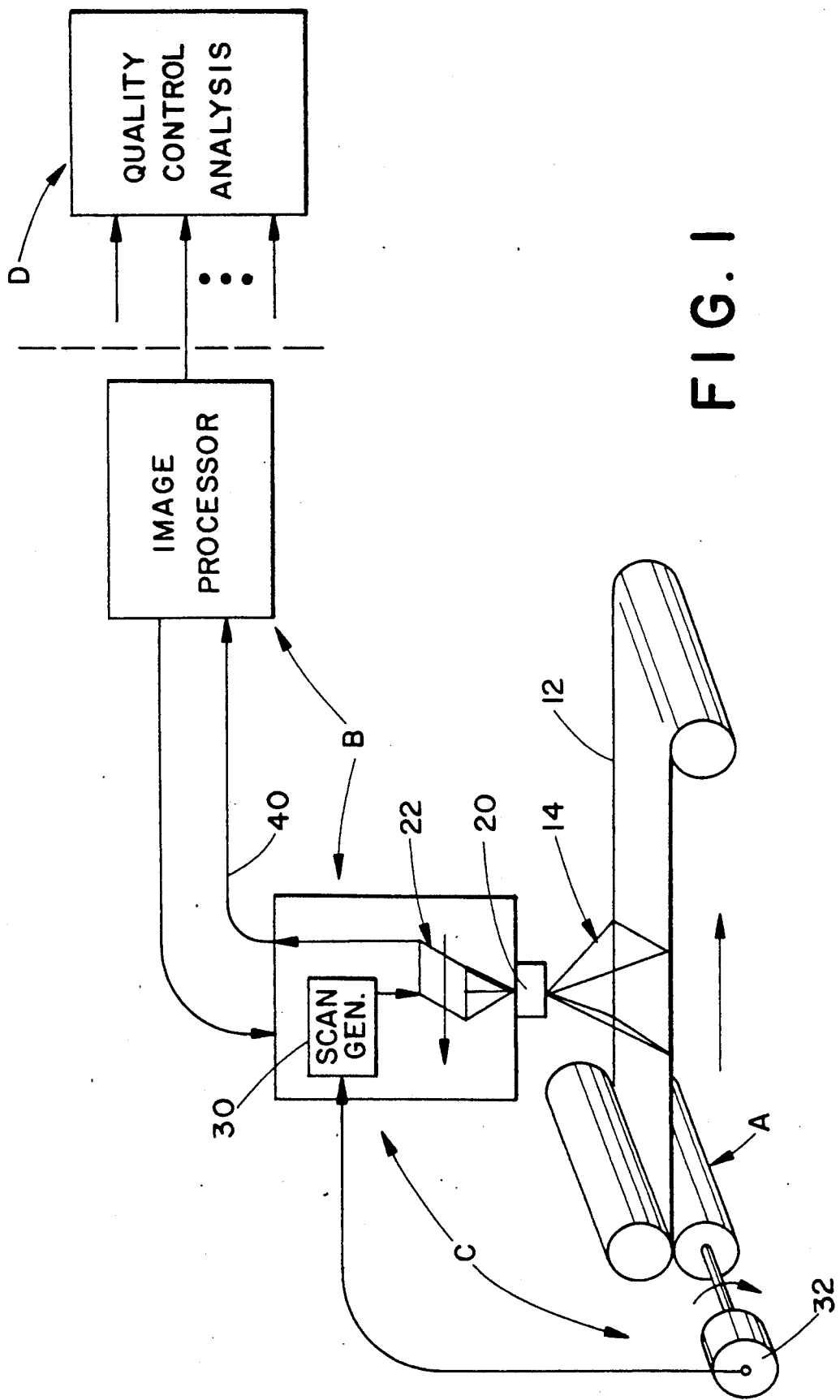
FIG. 1 is a diagrammatic illustration of a TDI camera and quality control system in accordance with the present invention.

With reference to FIG. 1, conveying means A moves a continuous web, a line object, or the like to be examined through an examination region at an adjustable or irregular speed. A CCD camera or opto-electrical transducer system B monitors the moving object by focusing an image of the moving object(s) on an opto-electric transducer. As the object moves, the image moves correspondingly along the transducer. A synchronizing control means C synchronizes and coordinates movement of the object and conversion of the image into an electronic video signal by the camera B. Specifically, the transducer samples the same element or pixel of an image several times. The synchronizing means causes the multiple samplings corresponding to the same pixel of the image but sampled at different sampling times and different regions of the transducer to be integrated. The synchronizing means preferably adapts the sampling of the transducer to movement of the object. However, in some applications it is advantageous to vary the speed of the object to match the sampling of the transducer. A quality control analysis means D analyses the video signal for flaws, defects, or other characteristics of the web and denotes their locations.

With continuing reference to FIG. 1 and further reference to FIG. 2A, the conveying means A includes a conventional conveyor 10 for a moving object 12 through the examination region 14. The nature of the conveyor is dependent on the object to be transported, as is known in the art. In the preferred embodiments, the conveyor includes rollers for a continuous web of floor coverings, wall paper, or other finished sheet goods. The examined subject may include sheets and films of plastics such as polyethylene, MYLAR, cellophane and vinyl, metals, glass, plywood, paper and other wood pulp products, fabrics, printing of newspapers, magazines, wallpaper, packaging, etc., lamination of plastics, composites, paper, etc., coating of plastics, metals, etc. with paint, magnetic particles, abrasives, adhesives, photographic emulsions, electrically conductive materials, etc., and embossing, cutting, slitting, perforating, etc. of any of the aforementioned raw or processed materials. Optionally, the conveyor may have pockets, recesses, or clamps for fixing the position of each received objects on the belt.

The camera B includes an optical system, such as a lens 20, which focuses photons of light radiation received from the examination region on a photosensitive area 22, preferably a bidirectional array of light sensitive elements. The lens focuses light emanating from the examination region continuously onto the light sensitive area or image section of the opto-electrical transducer. The resolution of the resultant image is determined by the number of light sensitive elements in each dimension. The more elements, the finer the resolution. A typical video camera might have a 244×610 element array. For color, a third of the elements have a green filter, a third have a blue filter, and a third have a red filter, or any other three color filter combination as is conventional in the art.

In conventional frame transfer CCD cameras, the data is periodically shifted in mass from the image section 22 to a light shielded storage section 24 during a vertical flyback period which erases or resets each element of the CCD image section. In the TDI mode, the vertical flyback signals are defeated, i.e. eliminated. The image section and storage section transfer are both connected to the synchronizing means C which step lines of pixels continuously at a variable line frequency rate to output registers 26. The synchronizing means controls the lines or rows of the photosensors 22, 24 in such a way that the accumulated charge is moved in synchronization with the light pattern arriving from the object being viewed. For example, when the web has a spot or blemish which passes through the examination region, the image of the spot is progressively transferred or shifted along the light sensitive area into the storage section 24. That is, as the object moves some small increment, the charge is shifted one row to follow the motion. If there are 100 rows of photoelements, then the total exposure time for each small area in the image will last 100 times as long as in a single-row imager. This permits the rows to be moved 100 times faster or for the intensity of the illumination to be reduced by 100. Interline-transfer CCD imagers as well as frame-transfer CCD imagers can also be used but require more complex support circuitry.

The charge values are shifted from row to row along the CCD array in precise synchronization with movement of the object being imaged and its image on the CCD array. For example, if the lens 20 focuses a 1 millimeter×1 millimeter area of the object on each element of the CCD array, then each time the object moves 1 millimeter, the pixel charge or integrated light value is shifted one row or line in the CCD array. In this manner, subsequent images on the CCD array superimpose directly on shifted previous images. By the time an image value or line of image values reaches the optically insensitive storage section 24 of the sensor, the optic information from the object has been integrated over the entire transfer period (1/10 second, for example). With the 244×610 CCD array, each pixel value represents the sum of light received at each of 244 CCD elements. The synchronization means C keeps monitored object movement and the image sensor transfer process in precise synchronization. In the preferred embodiment, the speed of the conveyor rollers, drive motors, or the like is converted by the synchronization means into clocking signals for the CCD array. Alternatively, signals from clocking electronics in the camera may be readjusted with variations in the speed of the conveyor.

In the time delayed integration mode, the pixel values in only the first line of the CCD array are refreshed each time. These pixel values are shifted along both the image and storage sections at a selectable speed and received light at each position is integrated. This is as opposed to the rapid transfer of pixel values from the image region to the storage region once per field in a frame transfer operation.

It is to be appreciated that the storage section 24 is unnecessary in the TDI mode and may be eliminated. Eliminating the storage section is advantageous in that it eliminates the storage section imposed delay between of the acquisition of each data line and its conversion into a line of video data. Although described in terms of a CCD image sensor array, it is to be appreciated that the summing of light intensity received at time delayed intervals at each pixel of a column in the TDI mode can be achieved in conjunction with other video image sensors beside CCD image sensor arrays. The data may even be integrated off the sensor array in a memory array which provides lines of integrated data values to the shift registers or other serializing means.

Figure 2B:
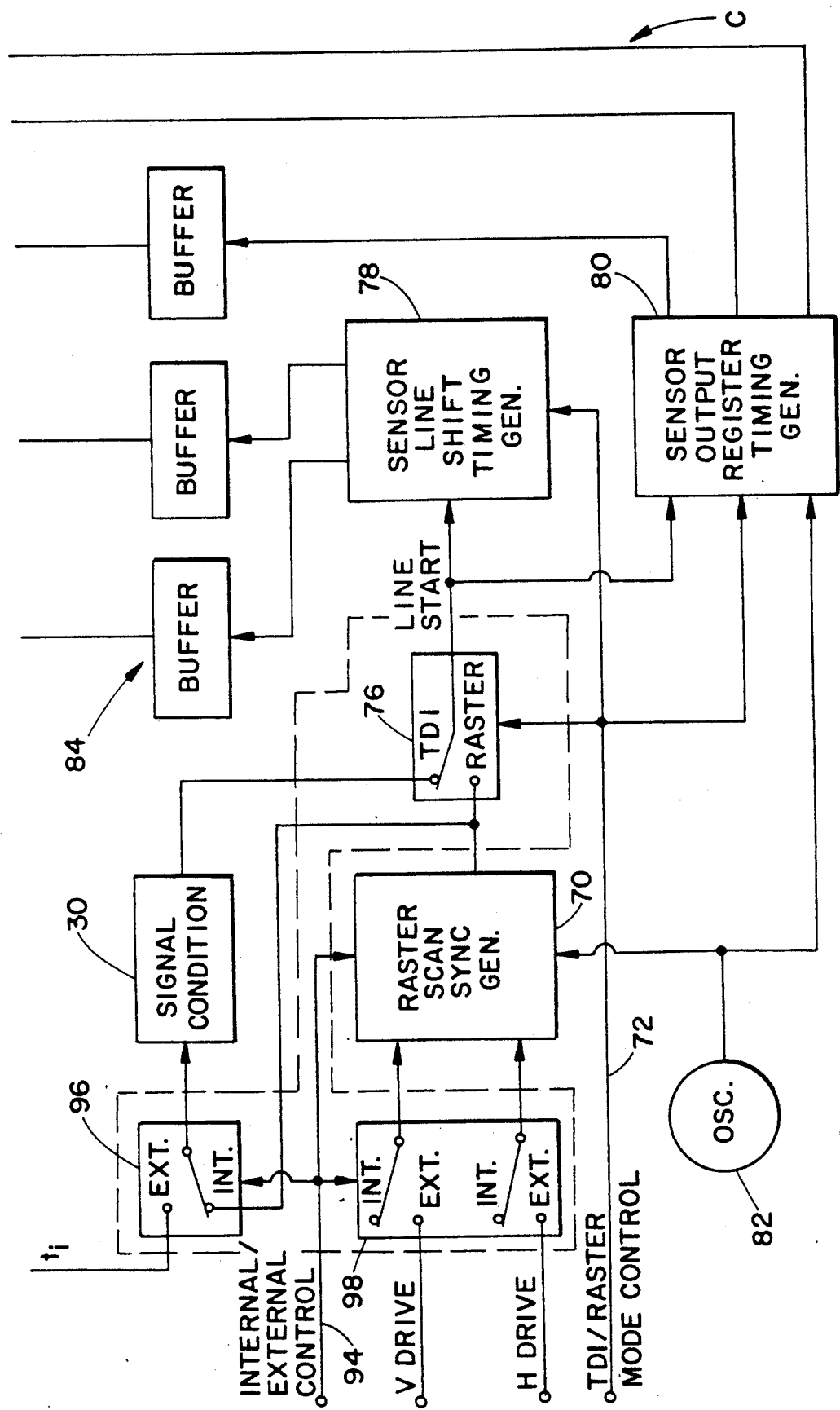

With reference to FIGS. 2A and 2B, a signal conditioner 30 receives a trigger signal $t_i$ from a conveyor speed sensor or tachometer 32 and produces clock pulses to clock the image sensor array at a corresponding rate. More specifically, the trigger signals control the frequency of an image section transfer clock or means 34, which supplies the clock signals to a light image sensor section control means 22a and a storage section control means 24a. The light image sensor control means 22a causes the charge of each image element or row of elements of the image section 22 to be shifted line by line. After about 244 pulses or shift commands in the illustrated 244 active line CCD image section embodiment, a line of charge values has been shifted 244 lines from the first line of the image section into the storage section 24.

The clocking signals are selected such that the image transfer is synchronized with the movement of the conveyor. The controller C conveys identical transfer clock pulses to the storage section control means 24a as sent to the image section control means 22a to cause the data from the storage section 24 to be shifted line by line into the shift registers means 26. To enable the camera to operate in either a conventional field mode or the time delay and integration mode, the storage section is the same size as the image section.

When using a color video image section, a red shift register 26r, a blue shift register 26b, and a green shift register 26g are provided. Alternatively, a color filter-free or black and white image section may be provided and a single black and white output shift register. Once a line of pixel or integrated light values have been transferred from the storage section 24 to the shift registers; the clocking means 34 sends higher speed three phase shift register clock signals to a shift register controller 26a. The shift registers serially step each charge or data value onto video signal output lines 40 before the next line is loaded into the shift registers from the storage section. Thus, between image or storage section transfer clock pulses, a number of shift register clock pulses equal to the number of elements per line are generated to clock out red, green, and blue (or black and white) output signals at a frequency and format that is compatible with EIA-170 television signal standards.

Feedback amplifiers 42 combine each of the three color output signals with a feedback signal which establishes a DC reference level to minimize the interfering effects of clock noise. A gain adjusting amplifier means 44 adjusts the gain of all three signal components correspondingly.

With reference to FIG. 3C, each color signal is processed by a like video channel 50, 50', and 50". The video channel includes an impedance adjusting amplifier 52 for providing a low impedance output signal. A band pass filter 54 removes any vestiges of clocking signal noise or the like. A user controlled gain amplifier 56 amplifies the signal from the band pass filter and passes it to a clamping means 58 which restores the DC video. At the end of each horizontal sweep line, the clamping means shorts to a DC reference level to restore a DC level that sets the black level of the resultant image. A synchronization information means 60 switches between lines to reference voltages to add blanking and horizontal synchronization information to the signal. By convention, the synchronization means 60 only adds synchronization information to one, generally the green, video component. A feedback circuit 62 feeds back a portion of the composite video signal to provide a phase sensitive detection of the clocking to establish the DC level that minimizes the clock noise.

Preferably, the feedback signal also is based on a single one of the components. The video processing circuitry is stable to better than one part in 256 to enable precision digitizing and digital signal processing of the resultant video signal.

The quality control analysis means D receives the composite video signal and operates on it in a manner that is appropriate to the quality control function undertaken. For example, the analysis means D may turn the composite signal into a man-readable video image. Alternately, the analysis means may examine components of the video signal corresponding to selected regions to determine whether they meet preselected characteristics relative to each other, preselected standards, or the like.

Looking by way of example to monitoring a continuous web of solid color material, the image of the web may change in gray scale or color relative to the rest of the web image. The change may be the result of color changes in the web or surface deformates that alter the amount of reflected light. The pixel values of the video signal of the web are compared with a preselected gray scale characteristic or value to determine if the web is deformed or damaged beyond selected tolerances. If the web has a repeating pattern, the image or video signal is compared with corresponding standards which change cyclically with the pattern to determine whether the web has been accurately processed. If the web is monitored in color, each image or pixel value of the video signal is compared with one of a plurality of colorimetric standards in accordance with a location within the pattern. Alternately, color or other physical parameters may be used to sort various types or grades of products. Numerous other sorting, quality control, and acceptance algorithms may be implemented as are appropriate to the requirements of the objects being examined.

With reference again to FIG. 2B, the synchronizing means C includes an internal raster scan sync generator means 70 which produces master timing signals for a raster-scan mode. The scan generator means may have either an internal crystal oscillator or external drive signals as its time base. A control line 72 receives input signals which enable the camera to operate in either the time delayed and integration (TDI) mode or the raster-scan mode. The mode selection signals control a switching means 74 including a first switch 76 which connects the output of either the raster-scan generator 70 or the process speed controlled clock signal from the signal conditioner to a sensor line shift timing generator 78 and an output register timing generator 80. A crystal oscillator 82 controls the timing of the output register timing generator and provides camera timing in the raster-scan mode. In this manner, the clocking of the shift register 26, hence, the video signal, is independent of process speed. The sensor line shift generating means 78 converts the received timing signals of the selected mode into four-phase clocks for the image and storage sections. The output register timing generating means 80 provides three phase clocks for reading out the pixel charges from the output register. The output register timing generating means also sends clamp timing signals to the clamping means 58 of the video channels and to the synchronization means 60. Buffers 84 condition the three and four phase clock pulses for use by the sensor and shift register controls. The three phase clock signals for the output shift registers 26 are controlled by the oscillator 80 in both modes.

For calibration, focusing, and alignment, the synchronizing means C is operated in an internally controlled TDI mode. More specifically, a calibration test chart 90 is mounted stationarily in the examination region 14. The calibration chart includes a plurality of parallel stripes 92, which stripes are aligned with the direction that an examined web moves through the examination region.

An internal/external control selection line 94 enables the operator to select between external control in which the timing control signals are externally supplied from the tachometer 32 or the like, and an internal control mode. The internal/external control line 94 is connected with a second switch 96 of the switching means 74 for switching the input of the signal conditioning means 30 between the external timing signal $t_i$ and an internal horizontal timing signal from the raster scan sync generating means 70. The internal/external control line further controls a third switch 98 of the mode switching means 74 which disconnects the raster scan generator 70 means from externally applied sources of vertical and horizontal drive signals. Passing the internal horizontal timing signal through the signal conditioner 30 assures that the sensor line shift timing generator 78 provides the same line timing in both internal and external TDI operation. Disconnecting the raster scan sync generator means from the external, vertical and horizontal drive signals assures that external signals are not supplied which causes a horizontal timing signal which exceeds the frequency of the conventional raster scan. Such high frequencies can cause jitter and other image degradation problems attributable to too high a horizontal timing speed.

The preferred embodiment can be operated in the above described time delay and integration mode, as a conventional video camera, or in the internally clocked time delay and integration mode. When the time delayed integration mode is selected, an appropriate input on the TDI/raster mode control input 72 causes the mode select means 74 to send the line start signals to the sensor line shift timing generator 78 and the sensor output register timing generator 80 and causes the sensor line timing generator 78 to send the four-phase TDI clock sequences to the image and storage section control means 22a, 24a. When the conventional frame mode is selected, the raster-scan sync generator 70 causes the sensor line generator to send conventional four-phase frame transfer clock signals or interline transfer clock signals.

Although only a single camera is illustrated for simplicity in the preferred embodiment, it is to be appreciated that multiple cameras may be used. For example, the camera may view adjoining sections across the web. Alternately, two cameras may view sections along the direction of movement, with the cameras coordinated to alternate lines. The multiple cameras are operated in their fixed frequency TDI mode on the test chart or a stationary web to align the viewed sections, align camera pixels, etc.

In yet another application, the camera may be cycled between the raster, internal and external controlled TDI modes to transfer different types of data. For example, the camera may alternately send images of people in the raster mode and documents in the TDI mode. This would permit the camera to function as a video phone and provide high resolution images or print outs of discussed documents or data.

The invention has been described with reference to the preferred embodiment. Obviously, modifications and alterations will occur to others upon reading and understanding the preceding detailed description. For example, as previously stated signals from the clocking controller electronics may be used to control the speed of the conveyor system. It is intended that the invention be construed as including all such alterations and modifications insofar as they come within the scope of the appended claims or the equivalents thereof.

Having thus described the preferred embodiment, the invention is now claimed to be:

1. A multimode camera comprising:
   a timing generating means for producing clock signals for controlling the shifting of lines of data values along an image sensor array;
   a switching means for switching one of external selectable frequency timing signals and internally generated fixed frequency timing signals from an internal sync generator means to the timing generating means; and,
   a lens for focusing radiation from a region of interest on the image sensing array.

2. The camera as set forth in claim 1 wherein the switching means includes means for selectively connecting (1) a raster scan sync generator means into communication with a timing signal generating means such as the camera operates in a standard raster scan mode, (2) the timing generating means with an external selectable frequency timing signal input, and (3) the raster scan sync generator means with the external timing signal input to provide fixed frequency timing signals thereto.

3. The camera as set forth in claim 2 wherein the external timing signal input is connected with a tachometer means for generating the external timing signal in accordance with a speed at which a conveyor is moving through the region of interest.

4. The camera as set forth in claim 3 wherein the image sensor array includes an array of photosensitive CCD elements that discharge charge values in accordance with received light radiation, the array has a multiplicity of lines of the photosensitive elements, which lines of photosensitive elements are clocked to shift lines of the charge values along the array by the clock signals from the timing generating means.

5. A camera system comprising:
   a conveying means for conveying at least one item to be examined through an examination region;
   a speed-dependent timing signal means for generating a speed-dependent timing signal that varies in accordance with a speed of the conveying means through the examination region;
   a lens which focuses photons from the examination region on at least a portion of an image sensor array, which array is defined by lines and columns of photosensitive elements;
   a timing generator means for controlling timing of integrating photons received at photosensitive elements of each column, the timing means being operatively connected with the speed-dependent timing signal means such that the timing means variably controls a time duration between integrations of photons along the columns in accordance with the speed-dependent timing signal such that as a given point on the conveying means moves through the examination region, the photons emanating therefrom and impinging sequentially on the photosensitive elements of the column are integrated.

6. The camera system as set forth in claim 5 further including a switching means for selectively switching the timing means between the speed-dependent timing signal means and a fixed frequency timing signal means.

7. The camera system as set forth in claim 6 further including a test chart disposed in the examination region when the switching means connects the timing means with the fixed frequency signal means, the test chart having a plurality of stripes extending parallel to a direction of conveyor means movement.

8. The camera system as set forth in claim 5 wherein the image sensor array is a CCD array and wherein the lens focuses light photons from a portion of an object moving through the examination region on to a progression of pixels of a column of the CCD array and wherein the timing means shifts charges along the CCD array pixels such that a charge corresponding to the examined object portion is shifted along the CCD array at the same rate that the focused light photons from the object portion moves along the CCD array.

9. The camera system as set forth in claim 8 further including a switching means for selectively connecting the timing means with one of the speed-dependent timing signal means and a fixed frequency source.

10. The camera system as set forth in claim 9 further including:
    a raster scan sync generator for generating internal vertical and horizontal timing signals; and,
    a switching means for selectively switching the timing means among the raster scan sync generator means to operate the CCD array in a conventional raster scan mode, the speed-dependent timing signal means, and with the internal horizontal timing signal from the raster scan sync generator such that charge values are shifted along the CCD array at a corresponding constant rate.

11. A multimode CCD camera comprising:
    a CCD array having a plurality of lines of light sensitive elements for accumulating lines of pixel values each indicative of an accumulated amount of light received;

a lens means for focusing light from a region of interest on the CCD array;

a serializing means for serializing each line of pixel values from the CCD array into an output video signal;

a line shift means for shifting the lines of pixel values along the CCD array to the serializing means at a rate controlled by received timing signals;

a raster scan sync generating means for generating conventional raster scan timing signals including horizontal timing signals of a preselected frequency and vertical flyback timing signals;

a timing signal conditioning means for conditioning an externally generated timing signal of adjustable frequency for compatibility with the line shift timing means; and, a switching means for selectively switching one of (1) the raster scan sync generating means into electrical communication with the line shift means for providing horizontal and vertical flyback timing signals thereto such that the lines of pixel data are read from the CCD array in a conventional raster scan mode, (2) the signal conditioning means into electrical communication with an external source of adjustable frequency timing signals such that the lines of pixel data are shifted along the CCD array at a rate in accordance with the external timing signal, and (3) the signal conditioning means into electrical communication with raster scan sync generating means for receiving the horizontal timing signals therefrom such that the lines of pixel data are shifted along the CCD array at a rate fixed by the raster scan sync generating means.

12. A method of generating video signals, the method comprising:

fixedly disposing a test chart in an examination region, the test chart having a plurality of parallel stripes;

while the test chart is in the examination region;
clocking an image sensing array at a fixed rate such that lines of pixel data are shifted therealong and integrated at the fixed rate,
serially reading the lines of data from the array, converting the lines into a video calibration signal,
adjusting at least one of focus, alignment, and calibration in accordance with the video calibration signal;

removing the test chart and moving a conveying means through the examination region in a direction parallel to the test chart stripes;

monitoring a speed of movement of the conveying means through the examination region and clocking the image sensing array in accordance therewith; and, reading out the lines of data from the array and converting the lines of data into a video signal.

* * * * *